United States Patent

Fischer et al.

Patent Number: 6,107,451
Date of Patent: Aug. 22, 2000

[54] HARDENER FOR ANHYDRIDE GROUP-CONTAINING POLYMERS

[75] Inventors: Walter Fischer, Reinach; Alex Wegmann, Allschwil, both of Switzerland

[73] Assignee: CIBA Specialty Chemicals Corp., Tarrytown, N.Y.

[21] Appl. No.: 09/177,141

[22] Filed: Oct. 21, 1998

[30] Foreign Application Priority Data

Oct. 23, 1997 [CH] Switzerland .............................. 2465/97

[51] Int. Cl.[7] ..................................................... C08G 69/26
[52] U.S. Cl. ............................ 528/335; 525/64; 525/293; 528/492
[58] Field of Search ..................... 528/335, 492; 525/64, 293

[56] References Cited

U.S. PATENT DOCUMENTS

| | | |
|---|---|---|
| 3,668,183 | 6/1972 | Hoy et al. |
| 4,089,845 | 5/1978 | Haug et al. ............................. 260/78 |
| 4,291,146 | 9/1981 | Haug ....................................... 528/119 |
| 5,151,470 | 9/1992 | Sanders et al. ........................ 525/407 |
| 5,633,341 | 5/1997 | Abend ..................................... 528/335 |
| 5,821,318 | 10/1998 | Fischer .................................... 528/93 |
| 5,844,047 | 12/1998 | Abend ................................... 525/327.7 |

FOREIGN PATENT DOCUMENTS

| | | |
|---|---|---|
| 125275 | of 0000 | Germany . |
| 123809 | 1/1977 | Germany . |
| 135730 | 5/1979 | Germany . |
| 144419 | 10/1980 | Germany . |

OTHER PUBLICATIONS

Derwent Abstr. 58133B/32 for DL 135730.
Derwent Abstr. 84491 C/48 for DL 144419.

*Primary Examiner*—Ana Woodward
*Attorney, Agent, or Firm*—Michele A. Kovaleski

[57] ABSTRACT

A curable composition consisting of at least 2 components (a) and (b), wherein (a) is a liquid oligomer or polymer having a molecular weight of 200–50,000 and containing dicarboxylic anhydride groups, and (b) is a compound of formula I

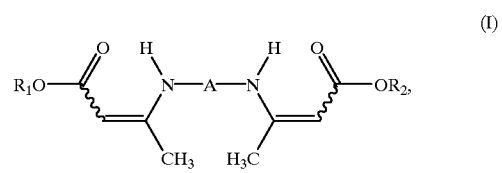

wherein A is linear or branched $C_2$–$C_{20}$alkylene, $C_5$–$C_7$cycloalkylene, $C_7$–$C_{10}$bicycloalkylene, or $C_1$–$C_{30}$alkylene containing one or more than one $C_5$–$C_7$cycloalkylene group or $C_7$–$C_{30}$bicycloalkylene group in the main or side chain, which cycloalkylene and bicycloalkylene groups can be unsubstituted or substituted by one or several $C_1$–$C_6$alkyl groups, and $R_1$ and $R_2$ are independently of each other $C_1$–$C_{18}$alkyl, $C_4$–$C_{10}$cycloalkyl or $C_7$–$C_{24}$-aralkyl, which cycloalkyl and aralkyl groups can be unsubstituted or substituted by one or more than one $C_1$–$C_6$alkyl group, has a long pot life at room temperature and is suitable for the preparation of moulded articles, primers and insulating layers.

9 Claims, No Drawings

HARDENER FOR ANHYDRIDE GROUP-CONTAINING POLYMERS

The present invention relates to a curable composition consisting of a polyanhydride and an enamino ester, to crosslinked products produced from these compositions, to a process for their production as well as to certain enamino esters.

WO 94/04624 describes liquid polymers containing dicarboxylic anhydride groups which can be cured with sterically hindered amines at room temperature and which are suitable for the formulation of reactive adhesives, sealants, coatings and casting compounds. The cross-linked products prepared from these mixtures are distinguished by high mechanical strength combined with high initial tear strength and tear propagation resistance. However, these products are typical 2-component systems, i.e. resin and hardener are stored separately and are mixed only shortly before application. As the components cure very rapidly after being mixed, the pot life of these systems is insufficient for certain applications.

It is the object of this invention to provide a curable system of high latency based on polymers containing dicarboxylic anhydride groups; i.e. the mixture of resin and hardener should have a sufficiently long pot life at room temperature but, if required, should also be capable of being cured within a short time by heating or by the action of moisture.

It has now been found that under exclusion of moisture certain enamino esters form stable mixtures with anhydride group-containing polymers, which mixtures can then be cured by the action of atmospheric humidity even at relatively low temperatures.

This invention relates to a curable composition consisting of at least 2 components (a) and (b), wherein
(a) is a liquid oligomer or polymer having a molecular weight of 200–50,000 and containing dicarboxylic anhydride groups, and
(b) is a compound of formula I

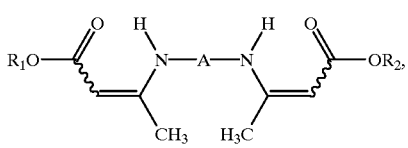

(I)

wherein A is linear or branched $C_2$–$C_{20}$alkylene, $C_5$–$C_7$cycloalkylene, $C_7$–$C_{10}$bicycloalkylene, or $C_1$–$C_{30}$alkylene containing one or more than one $C_5$–$C_7$cycloalkylene group or $C_7$–$C_{10}$bicycloalkylene group in the main or side chain, which cycloalkylene and bicycloalkylene groups can be unsubstituted or substituted by one or several $C_1$–$C_6$alkyl groups, and $R_1$ and $R_2$ are independently of each other $C_1$–$C_{18}$alkyl, $C_4$–$C_{10}$cycloalkyl or $C_7$–$C_{24}$-aralkyl, which cycloalkyl and aralkyl groups can be unsubstituted or substituted by one or more than one $C_1$–$C_6$alkyl group.

The representation of a chemical bond by a jagged line

~~~ in formula I and in the subsequent formulae means that the structural formula includes both geometrical isomers (E- and Z-isomers).

Examples of alkyl are methyl, ethyl, isopropyl, n-propyl, n-butyl, isobutyl, sec-butyl, tert-butyl and the different isomeric pentyl, hexyl, heptyl, octyl, nonyl, decyl, undecyl, dodecyl, tridecyl, tetradecyl, pentadecyl, hexadecyl, heptadecyl and octadecyl groups.

Cycloalkyl is preferably $C_5$–$C_8$Cycloalkyl, particularly preferably $C_5$- or $C_6$cycloalkyl. Some examples are cyclopentyl, methylcyclopentyl, cyclohexyl, cycloheptyl and cyclooctyl.

Aralkyl preferably contains 7 to 12 carbon atoms and, particularly preferably, 7 to 10 carbon atoms. Aralkyl may be, for example, benzyl, phenethyl, 3-phenylpropyl, α-methylbenzyl, 4-phenylbutyl and α,α-dimethylbenzyl.

Alkylene groups are typically propylene, ethylethylene, 1,3-butanediyl, 1,3-pentanediyl, 2-methyl-1,5-pentanediyl, 2,2,4-trimethyl-1,6-hexanediyl and 2,4,4-trimethyl-1,6-hexanediyl.

Examples of cycloalkylene are 1,3-cyclopentylene, 4-methyl-1,3-cyclopentylene, 1,3-cyclohexylene, 1,4-cyclohexylene and 4-methyl-1,3-cyclohexylene.

Bicycloalkylene groups are derived from bicyclic compounds such as norbornane, norbornadiene or norcarane. Examples of such bicycloalkylene groups are 2,5-norbornanediyl, 2,6-norbornanediyl, 7,7-dimethyl-2,5-norbornanediyl and 7,7-dimethyl-2,6-norbornanediyl. "$C_1$–$C_{30}$Alkylene containing one or more than one $C_5$–$C_7$cycloalkylene group or $C_7$–$C_{10}$bicycloalkylene group in the main or side chain" are divalent radicals which are derived from alkyl-substituted cycloalkanes and bicycloalkanes. Examples of such radicals are cyclohexane-1,3-dimethylene, cyclohexane-1,4-dimethylene, 3-methylene-3,5,5-trimethylcyclohexylene (isophorone), norbornane-2,5-dimethylene, norbornane-2,6-dimethylene, 7,7-dimethylnorbornane-2,5-dimethylene and 7,7-dimethylnorbornane-2,6-dimethylene.

Suitable polymers containing anhydride groups according to component (a) are known, inter alia, from WO 94/04624. Said polymers are polymers which are liquid at room temperature or copolymers having a molecular weight of up to 50,000, wherein the dicarboxylic anhydride groups may be distributed randomly or regularly over the molecule. The anhydride groups can be introduced by the copolymerisation of olefinically unsaturated compounds and unsaturated dicarboxylic anhydrides or by the addition of unsaturated anhydrides to polymers containing individual or conjugated double bonds, or by graft reactions.

Component (a) is preferably
a copolymer consisting of an unsaturated dicarboxylic anhydride and of one or more than one olefinically unsaturated monomer,
an addition product obtainable by reacting an unsaturated dicarboxylic anhydride with a polymer containing individual or conjugated double bonds,
an addition product obtainable by reacting an unsaturated dicarboxylic anhydride with unsaturated degradation products of high molecular weight elastomers,
a graft polymer obtainable by radically reacting an unsaturated dicarboxylic anhydride with a liquid polymer containing unsaturated double bonds, or
a polymeric ester anhydride obtainable by esterifying polyols with trimellitic anhydride, pyromellitic anhydride, benzenetetracarboxylic dianhydride or benzophenonetetracarboxylic dianhydride.

Examples of such crosslinkable polymers are:
copolymers of maleic or itaconic anhydride with olefins, dienes, vinyl compounds, vinyl aromatic compounds, vinyl esters, vinyl ethers, acrylic and methacrylic compounds;

addition products of maleic or itaconic anhydride with polymers of butadiene or isoprene, with copolymers of butadiene or isoprene with cyclopentadiene, styrene, acrylonitrile, olefins of up to 12 carbon atoms, with esters of unsaturated fatty acids or with terpenes;

addition products of maleic or itaconic anhydride with liquid, unsaturated degradation products of high molecular weight elastomers, such as natural rubber, styrene/butadiene rubber, acrylonitrilebutadiene rubber or thermoplastic styrene/butadienelisoprene rubbers; graft polymers obtainable by addition of maleic or itaconic anhydride to ethylene/propyiene/diene rubber (EPDM), ethylene/vinyl acetate copolymers (EVA), polyolefins or acrylic polymers;

polymeric ester anhydrides obtainable by esterifying polyols, such as ethylene glycol, diethylene glycol, triethylene glycol or pentaerythritol, with trimellitic anhydride, pyromellitic anhydride, benzenetetracarboxylic dianhyd ride or benzophenonetetracarboxylic dianhydxride.

Component (a) is particularly preferably an adduct of maleic anhydride with polymers or copolymers of butadiene.

The novel curable compositions can also comprise mixtures of different crosslinkable polymers as component (a). In addition to anhydride groups, the preferred liquid polymers can also contain other functional groups, for example alkoxysilyl groups or carboxyl groups.

It is preferred to use as component (a) liquid polymers having a molecular weight of 2,000 to 30,000 which contain on average 1.5 to 10, preferably 1.8 to 8, anhydride groups per molecule.

The acid number of the anhydride group-containing polymers is preferably from 15 to 150 mg KOH/g, more preferably from 20 to 100 mg KOH/g.

Component (a) may advantageously consist of mixtures of anhydride-containing polymers having different average molecular weights and, optionally, different numbers of anhydride groups per molecule. Alternatively, it is possible to use mixtures of polyfunctional anhydride group-containing polymers and monofunctional anhydride group-containing polymers, preferably low-molecular anhydride group-containing polymers. However, the mixtures should contain an average of at least 1.5 anhydride groups per molecule.

DE-A-25 29 092 discloses enamino esters of formula I and a process for their preparation.

In the curable compositions of this invention it is preferred to use a compound of formula I, wherein $R_1$ and $R_2$ are each independently of the other $C_1$–$C_4$alkyl or benzyl.

Other preferred compounds are those of formula I, wherein A is branched $C_5$–$C_{10}$alkylene, alkylated cyclohexylene or $C_2$–$C_{10}$alkylene containing a 1,3-cyclohexylene, 2,5-norbornylene or 2,6-norbornylene group in the main chain.

Particularly preferred compounds of formula I are those, wherein A is 2-methyl-1,5-pentanediyl, 1,3-cyclohexanedimethylene, 3-methylene-3,5,5-trimethylcyclohexylene, 2,5-norbornanedimethylene or 2,6-norbornanedimethylene, and $R_1$ and $R_2$ are ethyl. These compounds are novel and are also a subject matter of this invention.

These novel compounds can also be prepared by known methods by reacting the corresponding diamines with acetoacetates.

As these enamino esters are liquid at room temperature, the use of solvents may be foregone both for storing and for application.

The amounts of components (a) and (b) used in the novel compositions can vary within a wide range.

It is preferred to use, based on the sum of components (a)+(b), 65.0–99.9% by weight, more preferably 70.0–98.0% by weight, particularly preferably 80.0–95.0% by weight, of component (a), and 0.1–35.0% by weight, preferably 2.0–30.0% by weight, particularly preferably 5.0–20.0% by weight, of component (b).

The stoichiometric ratio of anhydride groups and secondary amino groups is preferably chosen such that there are 1.2–6.0, more preferably 1.4–4.0, equivalents of anhydride groups per 1 mol of a compound of formula I.

If convenient, curing accelerators may be added to the novel curable compositions, which accelerators catalyse the reacton of the anhydride groups with the amino groups. Suitable accelerators are, for example, tertiary amines, such as benzyldimethylamine, or imidazoles, such as imidazole, 1-methyl imidazole or 2-ethyl-4-methylimidazole.

The curable mixtures may additionally contain fillers, such as metal powder, wood flour, glass powder, glass beads, semimetal oxides and metal oxides, for example $SiO_2$ (aerosils, quartz, quartz powder, synthetic silica flour), corundum and titanium oxide, semimetal nitrides and metal nitrides, for example silicium nitride, boron nitride and aluminium nitride, semimetal carbide s and metal carbides (SiC), metal carbonates (dolomite, chalk, $CaCO_3$), metal sulfate (baryte, gypsum), mineral powders and natural or synthetic minerals mainly from the silicate series, for example zeolites (in particular molecular sieves), talcum, mica, kaolin, wollastonite, bentonite and others.

In addition to the above fillers, the curable mixtures can contain other customary additives, for example antioxidants, light stabilisers, plasticisers, colourants, pigments, thixotropic agents, toughness improvers, antifoams, antistatic agents, lubricants and demoulding assistants.

The novel mixture consisting of anhydride group-containing polymer and enamino ester is storage-stable for a prolonged period of time under exclusion of moisture; i.e. it may in principle also be used as a latent 1-component system. In this case the crosslinking process needs to be initiated by supply of moisture (atmospheric humidity being sufficient in most cases) and/or by heat.

However, the use as a 2-component system is preferred, resin and hardener component being stored separately and being mixed only immediately before application. Even after mixing the two components in air (i.e. in the presence of atmospheric humidity) the curing reaction proceeds relatively slowly at room temperature so that the pot life of the novel mixtures is sufficiently long for a wide range of applications.

The mixing and subsequent curing of the components (a) and (b) is conveniently carried out in the temperature range from −10° C. to +80° C., preferably from 0° C. to 50° C. Even at temperatures in the range from 0° C. to 15° C., the crosslinking reaction usually proceeds quantitatively within one day.

The components can be mixed by hand or using static or dynamic mixers. Especially in the case of highly viscous polymers of high molecular weight it is advisable to use static or dynamic mixers for processing since this substantially prevents the absorption of air in the cross-linking product.

In another of its aspects, this invention relates to a process for the preparation of crosslinked products, which comprises mixing the above-defined components (a) and (b) and curing them in the presence of moisture in the temperature range from −10° C. to +80° C.

This invention also relates to the products prepared by this process.

The properties of the crosslinked compositions can be selectively controlled by the skilled person and depend, amongst other factors, on the polymer content, on the anhydride content of the polymer, on the degree of polymerisation, on the proportion of comonomer, on the anhydride group content in relation to the content of secondary amino groups, and on the type of enamino ester. The resulting crosslinked products are very soft to hard compositions having different mechanical properties.

The enamino esters of formula I are suitable as curing agents not only for anhydride group-containing polymers but also for other reactive resins, such as epoxy resins and polyisocyanate resins.

This invention thus also relates to the use of compounds of formula I as hardeners for epoxy resins, polyisocyanate resins and, especially, for anhydride group-containing polymers.

The novel curable compositions are particularly suitable for use as surface coating materials, anti-slip coatings, sealants and casting compositions. The cured products are used as moulded articles, primers and insulating layers.

The invention is illustrated by the following Examples.

I. WORKING EXAMPLES

I.1. N,N'-4-methyl-1,3-cyclohexylenebis(3-aminocrotonic acid ethyl ester)

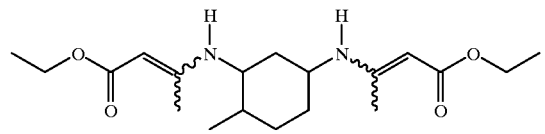

101.5 g of ethyl acetoacetate are added dropwise over one hour to a solution of 50 g of 1,3-diamino-4-methylcyclohexane, the temperature being kept, if required, below 35° C. by slight cooling. The mixture is left standing for 18 h at room temperature and is then dried with anhydrous potassium carbonate and filtered. The filtrate is concentrated under vacuum, affording 135.47 g of a yellowish oil which, according to $^{1}$H-NMR spectrum, consists of the cis-transisomers of the above structure.

I.2. N,N'-2-methyl-1,5-pentanediylbis(3-aminocrotonic acid ethyl ester)

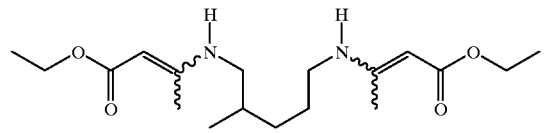

In analogy to Example I.1., 5 g of 1,5-diamino-2-methylpentane are reacted with 11.2 g of ethyl acetoacetate, giving 14.62 g of product.

I.3. N,N'-2,2,4-trimethyl-1,6-hexanediylbis(3-aminocrotonic acid ethyl ester) and N,N'-2,4,4-trimethyl-1,6-hexanediylbis(3-aminocrotonic acid ethyl ester)

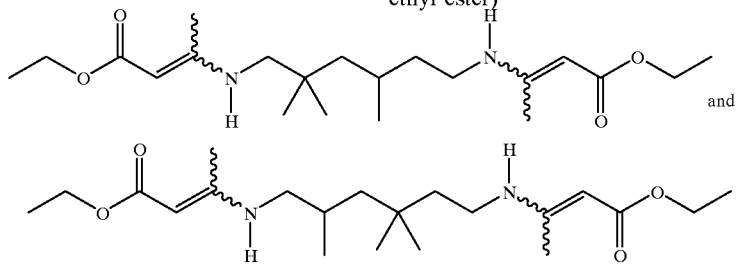

and

In analogy to Example I.1, 50 g of an isomer mixture of 1,6-diamino-2,2,4-trimethylhexane and 1,6-diamino-2,4,4-trimethylhexane are reacted with 82.22 g of ethyl acetoacetate, giving 119.37 g (98.8%) of the above isomer mixture.

I.4. N,N'-norbornane-2,5-dimethylenebis(3-aminocrotonic acid ethyl ester) and N,N'-norbornane-2,6-dimethylenebis(3-aminocrotonic acid ethyl ester)

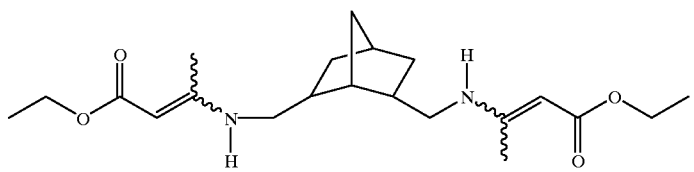

-continued

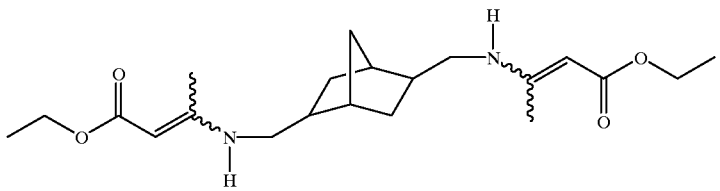

In analogy to Example I.1., 60 g of an isomer mixture of 2,5-bis(aminomethyl)norbornane and 2,6-bis(aminomethyl)norbornane are reacted with 101.23 g of ethyl acetoacetate, giving 146.9 g of the above isomer mixture (according to $^1$H-NMR 2,5- and 2,6-isomers and endo-exo-isomers).

I.5. N,N'-cyclohexane-1,3-dimethylenebis(3-aminocrotonic acid ethyl ester)

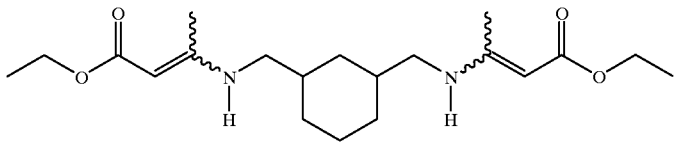

In analogy to Example I.1., 50 g of 1,3-bis(aminomethyl)cyclohexane are reacted with 91.49 g of ethyl acetoacetate, giving 127.8 g (99.1%) of a product which, according to $^1$H-NMR, consists of the cis-trans-isomer mixture of the above structure.

I.6. N,N'-3-methylene-3,5,5-trimethylcyclohexvlenebis(3-aminocrotonic acid ethyl ester)

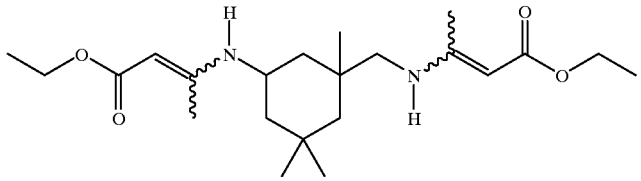

In analogy to Example I.1., 50 g of isophorone diamine are reacted with 76.42 g of ethyl acetoacetate, giving 115.72 g (99.9%) of a product which, according to $^1$H-NMR, consists of the cis-trans-isomer mixture of the above structure.

II. USE EXAMPLES

In the following Examples, component (a) is a liquid graft copolymer (polyanhydride 1) which is prepared by radical reaction of polybutadiene (average molecular weight: 5,000) with 10% by weight (based on the polybutadiene used) of maleic anhydride.

Example II.1.:

A mixture consisting of 15.85 g of polyanhydride 1 and 2.5 g of the enamino ester prepared according to Example I.1. is applied to glass and steel plates using a 200 μm coating knife. An initial orange colouration disappears again after a short time. The excellent flow of this mixture results in smooth, clear and lustrous layers which cure within a few hours at room temperature. The pendulum hardness in accordance with Persoz is 51 s after 1 day at room temperature and increases to 55 s after 7 days and to 65 s after 1 month. These values show that the films are almost completely cured already after one day and reflect the high flexibility of the cured films.

The remaining reaction composition which was not applied as layers stays liquid for several days except for a moisture-dependent skin formation on its surface. This demonstrates the high latency of this system.

If the same mixture is cured at 5° C., the pendulum hardness in accordance with Persoz is 27 s after 7 days. The same value is found after one month.

Example II.2.:

In analogy to Example II.1., 8.21 g of polyanhydride 1 are reacted with 1.25 g of the enamino ester prepared according to Example I.2. Flow and flexibility of the cured film are similar to those of Example II.1. The coating cures completely within a few hours, the pot life of the reaction composition under exclusion of moisture being several days. The pendulum hardnesses measured at different intervals during storage at RT (room temperature) and at 5 ° C. are listed in Table 1.

TABLE 1

| | Pendulum hardness acc. to Persoz Storage at RT | Pendulum hardness acc. to Persoz Storage at 5° C. |
|---|---|---|
| 1 day | 38 s | |
| 1 week | 41 s | 34 s |
| 1 month | 40 s | 28 s |

Example II.3.:

In analogy to Example II.1., 44.3 g of polyanhydride 1 are cured with 7.5 g of the enamino ester prepared according to Example I.4. Flow and flexibility of the cured film are similar to those of Example II.1. The coating cures completely within a few hours and the pot life of the reaction compositions under exclusion of moisture is several days. The pendulum hardnesses measured at different intervals during storage at RT (room temperature) and at 5° C. are listed in Table 2.

TABLE 2

| | Pendulum hardness acc. to Persoz Storage at RT | Pendulum hardness acc. to Persoz Storage at 5° C. |
|---|---|---|
| 1 day | 57 s | |
| 1 week | 69 s | 57 s |
| 1 month | 58 s | 53 s |

Example II.4.:

In analogy to Example II.1., 8.5 g of polyanhydride 1 are cured with 1.5 g of the enamino ester prepared according to Example I.6. Flow and flexibility of the cured film are similar to those of Example II.1. The coating cures completely within a few hours and the pot life of the reaction composition under exclusion of moisture is several days. The pendulum hardnesses measured at different intervals during storage at RT (room temperature) and at 5° C. are listed in Table 3.

TABLE 3

| | Pendulum hardness acc. to Persoz Storage at RT | Pendulum hardness acc. to Persoz Storage at 5° C. |
|---|---|---|
| 1 day | 47 s | |
| 1 week | 45 s | 40 s |
| 1 month | 48 s | 31 s |

What is claimed is:

1. The curable composition, which consists of
   (a) a liquid oligomer or liquid polymer having a molecular weight of 200–50,000 and containing dicarboxylic anhydride groups selected from the group consisting of
      a copolymer consisting of an unsaturated dicarboxylic anhydride and of one or more than one olefinically unsaturated monomer,
      an addition product obtained by reacting an unsaturated dicarboxylic anhydride with a polymer containing individual or conjugated double bonds,
      an addition product obtained by reacting an unsaturated dicarboxylic anhydride with unsaturated degradation products of high molecular weight elastomers,
      a graft polymer obtained by radically reacting an unsaturated dicarboxylic anhydride with a liquid polymer containing unsaturated double bonds, and
      a polymeric ester anhydride obtained by esterifying polyols with trimellitic anhydride, pyromellitic anhydride, benzenetetracarboxylic dianhydride or benzophenontetracarboxylic dianhydride, and
   (b) a compound of formula I

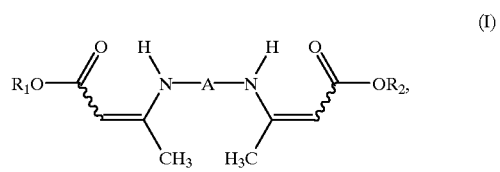

wherein A is linear or branched $C_2$–$C_{20}$alkylene; $C_5$–$C_7$cycloalkylene which is unsubstituted or substituted by one or more $C_1$–$C_6$alkyl groups; $C_7$–$C_{10}$bicycloalkylene which is unsubstituted or substituted by one or more $C_1$–$C_6$alkyl groups; or $C_1$–$C_{30}$alkylene containing one or more than one $C_5$–$C_7$cycloalkylene group or $C_7$–$C_{10}$bicycloalkylene group in the main or side chain, which cycloalkylene and bicycloalkylene groups are unsubstituted or substitltd by one or several $C_1$–$C_6$alkyl groups; and $R_1$ and $R_2$ are independently of each other $C_1$–$C_{18}$alkyl, $C_4$–$C_{10}$cycloalkyl or $C_7$–$C_{24}$aralkyl, which cycloalkyl and aralkyl groups can be unsubstituted or substituted by one or more than one $C_1$–$C_6$alkyl group.

2. The curable composition according to claim 1, wherein component (a) is an adduct of maleic anhydride with polymers or copolymers of butadiene.

3. The curable composition according to claim 1, wherein component (b) is a compound of formula I, wherein $R_1$ and $R_2$ are independently of each other $C_1$–$C_4$alkyl or benzyl.

4. The curable composition according to claim 1, wherein component (b) is a compound of formula I, wherein A is branched $C_5$–$C_{10}$alkylene, alkylated cyclohexylene or $C_2$–$C_{10}$alkylene containing a 1,3-cyclohexylene, 2,5-norbornylene or 2,6-norbornytene group in the main chain.

5. The curable composition according to claim 1, which comprises, based on the sum of the components (a)+(b), 65.0–99.9% by weight of component (a) and 0.1–35.0% by weight of component (b).

6. The curable composition according to claim 1, wherein the components (a) and (b) are present in such amounts that there are 1.2–6.0 equivalents of anhydride groups per 1 mol of a compound of formula I.

7. The compound of formula I according to claim 1, wherein A is 2-methyl-1,5-pentanediyl, 1,3-cyclohexanedimethylene, 3-methylene-3,5,5-trimethylcyclohexylene, 2,5-norbornanedimethylene or 2,6-norbornanedimethylene, and $R_1$ and $R_2$ are ethyl.

8. The process for the preparation of crosslinked products, which comprises mixing the components (a) and (b) according to claim 1 and curing them in the presence of moisture in the temperature range from −10° C. to +80° C.

9. The crosslinked products prepared according to the process claimed in claim 8.

* * * * *